United States Patent [19]

Umezawa et al.

[11] Patent Number: 4,833,241

[45] Date of Patent: May 23, 1989

[54] ANTHRACYCLINE COMPOUND

[75] Inventors: Hamao Umezawa, Tokyo; Hiroyuki Kawai; Shohachi Nakajima, both of Maebashi, all of Japan

[73] Assignee: Kirin Beer Kabushiki Kaisha, Tokyo, Japan

[21] Appl. No.: 68,629

[22] Filed: Jun. 30, 1987

[30] Foreign Application Priority Data

Jul. 4, 1986 [JP] Japan ................................. 61-157357

[51] Int. Cl.⁴ .............................................. C07H 15/24
[52] U.S. Cl. ...................................................... 536/6.4
[58] Field of Search ......................................... 536/6.4

[56] References Cited

U.S. PATENT DOCUMENTS 4,301,277 11/1981 Acton et al. .......................... 536/6.4
4,585,859 4/1986 Mosher et al. ....................... 536/6.4

Primary Examiner—Johnnie R. Brown
Assistant Examiner—Elli Peselev
Attorney, Agent, or Firm—Ladas & Parry

[57] ABSTRACT

Disclosed is an anthracycline compound of the following formula (I) or an acid addition salt thereof:

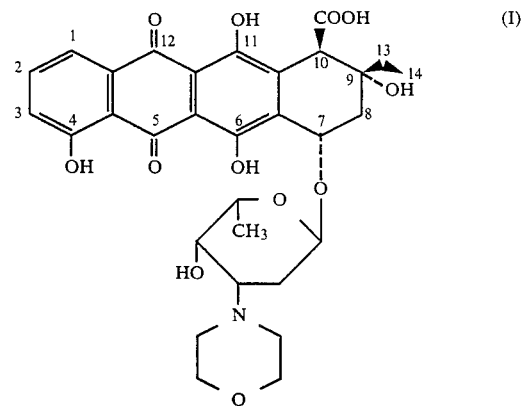

These compounds are useful as intermediates in the synthesis of an anthracycline compound, M-R20X or M-R20X2, which has antitumor activity.

1 Claim, No Drawings

ANTHRACYCLINE COMPOUND

BACKGROUND OF THE INVENTION

The present invention relates to an anthracycline compound, 3'-deamino-3'-(4-morpholinyl)-13-deoxo-10-hydroxycarbonylcarminomycin (hereinafter referred to as M-R20X3), and an acid addition salt thereof.

As novel anthracycline compounds having antitumor activity, 3'-deamino-3'-(4-morpholinyl)-13-deoxocarminomycin (hereinafter referred to as M-R20X) and 3'-deamino-3'-(4-morpholinyl)-13-deoxo-10-hydroxycarminomycin (hereinafter referred to as M-R20X2) were produced, for which a patent has already been applied (Japanese patent application No. 7196/1985). Both of these compounds are remarkably useful as antitumor substances and have physicochemical properties as well as physiological activities which will be set forth hereinlater. In Japanese patent appln. No. 7196/1985, M-R20X or M-R20X2 was produced by morpholinylation of 13-deoxocarminomycin (hereinafter referred to as R20X) or 13-deoxo-10-hydroxycarminomycin (hereinafter referred to as R20X2).

One of the co-inventors of the present invention has found in the culture broth of a mutant strain 3T-373 of *Streptomyces coeruleorubidus* ME130-A4 (FERM BP-165) the novel compound 13-deoxo-10-hydroxycarbonylcarminomycin (hereinafter referred to as R20X3) which can be a starting compound for the synthesis of the M-R20X3 of the present invention, and applied for a patent (Japanese patent laid-open pub. No. 8300/1985).

SUMMARY OF THE INVENTION

The present invention provides a novel anthracycline compound, M-R20X3, which is useful as an intermediate in the synthesis of M-R20X or M-R20X2.

More particularly, the M-R20X3 according to this invention is represented by the following formula:

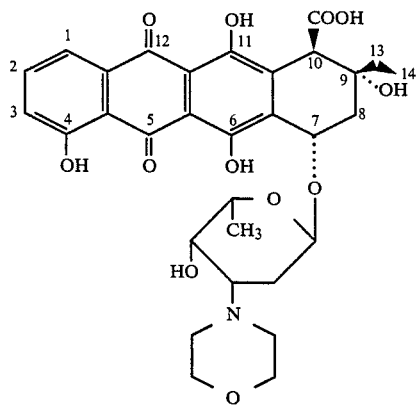

The present invention also relates to an acid addition salt of the above compound.

DETAILED DESCRIPTION OF THE INVENTION

M-R20X3

(1) Chemical structure

The M-R20X3 according to this invention has a chemical structure as shown by the above formula (I).

The present invention also provides an acid addition salt of the M-R20X3. Examples of such acids are inorganic acids such as hydrochloric acid, sulfuric acid and phosphoric acid, and organic acids such as acetic acid, propionic acid, maleic acid, oleic acid, palmitic acid, citric acid, succinic acid, tartaric acid, fumaric acid, glutamic acid, pantothenic acid and laurylsulfonic acid.

(2) Physicochemical properties

The physicochemical properties of the M-R20X3 are as follows.

(1) Melting point: 171° to 173° C.

(2) Specific rotatory power:
$[\alpha]_D^{25} = +163°$
(C=0.015, in methanol)

(3) Ultraviolet and visible absorption spectrum (in methanol):

| $\lambda_{max}$ nm($E_{1\ cm}^{1\%}$): | 234 (583) |
|---|---|
| | 257 (445) |
| | 462 (160) |
| | 493 (171) |
| | 528 (117) |

(4) Infrared absorption spectrum (KBr)(cm$^{-1}$):
1720, 1620

(5) Proton nuclear magnetic resonance spectrum (in deuterochloroform-deutero methanol):

| 1.07 (ppm) | (3H, t, J=6.0 Hz, H-14) |
|---|---|
| 1.29 | (3H, d, J=6.3 Hz, H-6') |
| 1.54 | (1H, m, H-13a) |
| 1.81 | (1H, m, H-13b) |
| 1.72–2.30 | (4H, m, H-2', H-8) |
| 2.35–2.55 | (5H, m, H-3'', H-5'', H-3') |
| 3.62 | (4H, m, H-2'', H-6'') |
| 3.64 | (1H, brs, H-4') |
| 4.00 | (1H, q, J=6.3 Hz, H-5') |
| 4.16 | (1H, s, H-10) |
| 5.15 | (1H, brs, H-7) |
| 5.44 | (1H, brs, H-1') |
| 7.26 | (1H, d, J=8.0 Hz, H-3) |
| 7.64 | (1H, dd, J=8.0, 8.0 Hz, H-2) |
| 7.81 | (1H, d, J=8.0 Hz, H-1) |

Since this compound is extremely labile, the measurements (1) through (4) were carried out quickly, and no decomposition was observed after the completion of the measurements.

The numbers added to the symbols in (5) indicate the positions of the hydrogen atoms bonded to the carbon atoms bearing the following numbers.

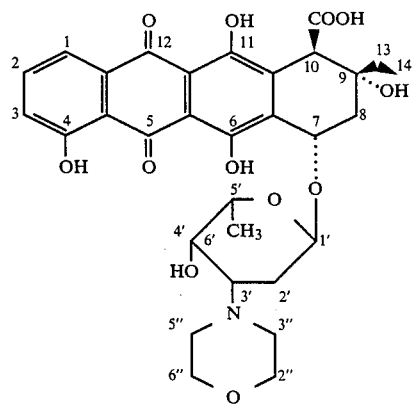

(6) Behavior as observed by thin-layer chromatography (on silica gel TLC plate 60F$_{254}$ supplied by Merck & Co., Inc.)
Chloroform: Methanol=10:1 RF=0.3

Production of M-R20X3

The M-R20X3 of the present invention can be produced by conversion of the amino group in R20X3 obtained by the cultivation of microorganisms into a morpholinyl group.

(1) R20X3

The R20X3 is a known substance and can be produced by the procedure described in Japanese patent laid-open pub. No. 8300/1985 mentioned previously.

The R20X3 can also be obtained from the culture of *Actinomadura roseoviolacea* 1029-AV1 (hereinafter referred to as strain R20) (as will be understood from Reference Examples described hereinlater).

This strain R20 was deposited on July 5, 1983 with the Fermentation Research Institute, Agency of Industrial Science and Technology, where it was assigned the accession number FERM BP-945 (FERM P-7138), and the microbiological characteristics thereof are set forth in detail in Japanese patent laid-open pub. No. 38391/1985.

(2) Conversion of amino group into morpholinyl group

The M-R20X3 of the present invention can be produced by the method which involves reacting R20X3 or an acid addition salt thereof with 2,2'-oxydiacetaldehyde represented by the following formula (II) (hereinafter referred to as Method A) or the method which involves reacting R20X3 or an acid addition salt thereof with bis-(2-haloethyl)ether represented by the formula (III):

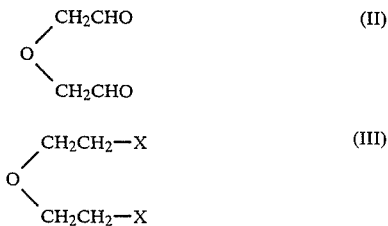

wherein X is a bromine atom or an iodine atom in the co-presence of a dehydrohalogenating agent (hereinafter referred to as Method B).

In the Method A, the compound (II) can be prepared from meso-erythritol by the procedure described in Carbohydrate Research Vol. 35, 195–202(1974).

The reaction of R20X3 or an acid addition salt thereof with the compound of the formula (II) is ordinarily carried out in a solvent. Examples of solvents that can be employed in the reaction are acetonitrile, methanol, ethanol, water, chloroform, dichloromethane, carbon tetrachloride, benzene, dioxane, and tetrahydrofuran, singly or in a mixture.

Preferably, this reaction is carried out in the presence of a reducing agent such as sodium borohydride (NaBH$_4$) or sodium cyanoborohydride (NaBH$_3$CN). The quantity of the reducing agent used is not critical, and the agent can be used in a quantity of at least 1 mol, preferably 1 to 5 mols, per mol of the R20X3.

The compound of the formula (II) is advantageously used in a rate of at least 1.5 mol, preferably at least 5 mols, and more preferably from 8 to 15 mols, per mol of the R20X3.

A suitable reaction temperature is generally in the range of from the solidifying point of the solvent employed to 50° C., a temperature around room temperature being particularly suitable.

Under the above stated reaction conditions, the reaction of converting the amino group into the morpholinyl group can be terminated within about 10 min. to 2 hours.

In the Method B, the R20X3 or an acid addition salt thereof is reacted with the compound of the formula (III) in the co-presence of a dehydrohalogenating agent under essentially the same conditions as are disclosed in Japanese patent laid-open pub. No. 163393/1982.

The reaction mixture obtained by the reaction of the R20X3 with the compound of the formula (II) or (III) can be purified to isolate M-R20X3 by a known purification procedure employed in the preparation of glycoside derivatives of anthracycline compounds, for example, chromatography using silica gel and the like.

The M-R20X3 of the formula (I) thus obtained can per se be converted into an acid addition salt thereof by a known method, for example, by treating the compound with any of the inorganic acids or organic acids as mentioned hereinbefore.

Uses of M-R20X3

M-R20X3 is useful as an intermediate in the synthesis of M-R20X or M-R20X2.

Methods by which M-R20X or M-R20X2 is obtained from M-R20X3 are as follows.

M-R20X2 and M-R20X can be obtained by adding to M-R20X3 an aprotic solvent such as acetone, dimethylformamide or acetonitrile and stirring the mixture at room temperature for at least 10 minutes; or by dissolving M-R20X3 in aqueous ammonia or a trialkylamine such as triethylamine, adding to the resulting solution an aprotic solvent such as acetone, dimethylformamide or acetonitrile in a volume at least twofold that of the aqueous ammonia or trialkylamine, and stirring the mixture at room temperature for at least 10 minutes.

Further, M-R20X2 and M-R20X can also be obtained by the above method without isolating and purifying M-R20X3.

More particularly, M-R20X and M-R20X2 can be obtained by carrying out the conversion reaction from the amino group into a morpholinyl group in the production of M-R20X3 in a suitable solvent such as methanol, acetonitrile or a chloroform-methanol mixture and, after concentration or immediately, applying the above mentioned method to the reaction mixture obtained.

The physiocochemical properties and main physiological activities of the M-R20X and M-R20X2 obtained in the manner described hereinbefore are as follows.

A. Physicochemical properties a. M-R20X (1) Appearance: Reddish brown powder
(2) Elementary analysis

|  | C | H | N | O |
|---|---|---|---|---|
| Found (%) | 62.98 | 6.31 | 2.40 | 28.31 |
| Calcd. (%) | 63.26 | 6.19 | 2.46 | 28.09 |

(3) Molecular weight: 569.6
(4) Melting point: 143°–144° C. (decomposed)
(5) Specific rotatory power:

$[\alpha]_D^{25} = +76°$
(C=0.05, in methanol)

(6) Ultraviolet and visible absorption spectrum:
(a) in methanol $\lambda_{max}$ nm ($E_{1\ cm}^{1\%}$)
234 (683), 252 (545)
292 (158), 464 (205),
492 (261), 508 (194),
524 (181), 575 (18)
(b) in acidic methanol $\lambda_{max}$ nm ($E_{1\ cm}^{1\%}$)
234 (783), 252 (612),
292 (192), 466 (233),
492 (315), 510 (227),
524 (202)
(c) in alkaline methanol $\lambda_{max}$ nm ($E_{1\ cm}^{1\%}$)
226 (422), 243 (653),
290 (166), 528 (126)
562 (192), 596 (162)

(7) Infrared absorption spectrum (KBr):
3350 cm$^{-1}$, 1600 cm$^{-1}$ (8) Proton nuclear magnetic resonance spectrum (in deuterochloroform):
(For the numbers indicating the positions of the hydrogen atoms, refer to those explained previously for M-R20X3.)

| | |
|---|---|
| 1.09 | (3H, t, J=7.9 Hz, H-13) |
| 1.40 | (3H, d, J=6.4 Hz, H-6') |
| 1.5–2.7 | (11H, m, H-8, H-13, H-2', H-3″, H-5″, H-3') |
| 2.58 | (1H, d, J=19.0 Hz, H-10a) |
| 2.97 | (1H, brs, 4'-OH) |
| 3.27 | (1H, d, J=19.0 Hz, H-10b) |
| 3.67 | (4H, m, H-2″, H-6″) |
| 3.70 | (1H, brs, H-4') |
| 4.13 | (1H, q, J=6.4 Hz, H-5') |
| 4.20 | (1H, s, 9-OH) |
| 5.23 | (1H, d, J=3.8 Hz, H-7) |
| 5.52 | (1H, d, J=2.9 Hz, H-1') |
| 7.31 | (1H, d, J=8.3 Hz, H-3) |
| 7.72 | (1H, dd, J=8.3 Hz, 8.3 Hz, H-2) |
| 7.89 | (1H, d, J=8.3 Hz, H-1) |
| 12.22 | (1H, s, 4-OH) |
| 12.95 | (1H, s, 6-OH) |
| 13.55 | (1H, s, 11-OH) |

(9) Rf Value (Silica gel plates 60F$_{254}$ supplied by Merck & Co., Inc. were used.):

| Developer | Rf Value |
|---|---|
| Chloroform:Methanol 10:1 | 0.42 |
| Chloroform:Methanol:Acetic acid 10:1:1 | 0.61 |
| Chloroform:Methanol:Triethylamine 10:1:1 | 0.72 |

(10) Solubility:
Soluble in acidic water, basic water, methanol, ethanol, propanol, acetone, ethyl acetate, and chloroform.
Insoluble in water, hexane, cyclohexane, diethyl ether, and petroleum ether.

b. M-R20X2
(1) Appearance: Brown powder
(2) Elementary analysis:

| | C | H | N | O |
|---|---|---|---|---|
| Found (%) | 61.32 | 6.30 | 2.26 | 30.12 |
| Calcd. (%) | 61.53 | 6.02 | 2.39 | 30.06 |

(3) Molecular weight: 585.6
(4) Melting point: 155°–157° C. (decomposed)
(5) Ultraviolet and visible absorption spectrum:
(a) in methanol $\lambda_{max}$ nm ($E_{1\ cm}^{1\%}$)
234 (821), 252 (478),
290 (153), 468 (241),
480 (263), 492 (295),
514 (216), 526 (196),
582 (17)
(b) in acidic methanol $\lambda_{max}$ nm ($E_{1\ cm}^{1\%}$)
234 (805), 252 (479),
290 (155), 468 (246),
480 (273), 492 (297),
512 (214), 526 (193)
(c) in alkaline methanol $\lambda_{max}$ nm ($E_{1\ cm}^{1\%}$)
242 (831), 292 (149),
534 (212), 564 (280),
600 (226)

(6) Specific rotatory power:
$[\alpha]_D^{20} = +306°$
(C=0.05, in CHCl$_3$)

(7) Infrared absorption spectrum (KBr):
3300 cm$^{-1}$, 1565 cm$^{-1}$ (8) Proton nuclear magnetic resonance spectrum (in deuterochloroform)
(For the numbers indicating the positions of the hydrogen atoms, refer to those explained previously for M-R20X3.)

| | |
|---|---|
| 1.12 | (3H, t, J=7.9 Hz, H-14) |
| 1.41 | (3H, d, J=6.4 Hz, H-6') |
| 1.75–1.92 | (4H, m, H-13, H-2') |
| 2.15 | (1H, dd, J=14.8, 3.0 Hz, H-8a) |
| 2.26 | (1H, d, J=14.8 Hz, H-8b) |
| 2.40, 2.53 | (5H, m, H-3″, H-5″, H-3') |
| 2.76 | (1H, d, J=4.5 Hz, 10-OH) |
| 2.97 | (1H, brs, 4'-OH) |
| 3.62 | (4H, m, H-2″, H-6″) |
| 3.70 | (1H, brs, H-4') |
| 3.97 | (1H, s, 9-OH) |
| 4.08 | (1H, q, J=6.4 Hz, H-5') |
| 4.91 | (1H, d, J=4.5 Hz, H-10) |
| 5.13 | (1H, d, J=3.0 Hz, H-7) |
| 5.51 | (1H, d, J=3.2 Hz, H-1') |
| 7.32 | (1H, d, J=8.0 Hz, H-3) |
| 7.72 | (1H, dd, J=8.0, 8.0 Hz, H-2) |
| 7.90 | (1H, d, J=8.0 Hz, H-1) |
| 12.15 | (1H, s, 4-OH) |
| 12.85 | (1H, s, 6-OH) |
| 13.73 | (1H, s, 11-OH) |

(9) Solubility:
Soluble in acidic water, basic water, methanol, ethanol, propanol, acetone, ethyl acetate, and chloroform.
Insoluble in water, hexane, cyclohexane, diethyl ether, and petroleum ether.

(10) Rf Value (Silica gel plates 60F$_{254}$ supplied by Merck & Co., Inc. were used.):

| Developer | Rf Value |
|---|---|
| Chloroform:Methanol 10:1 | 0.40 |
| Chloroform:Methanol:Acetic acid 10:1:1 | 0.59 |
| Chloroform:Methanol:Triethylamine 10:1:1 | 0.72 |

B. Physiological activities
a. Antitumor activity
Into CDF$_1$ mice were intraperitoneally transplanted P388 leukemia 1×10$^6$ cells/mouse as a suspension, and M-R20X or M-R20X2 was administered to the mice intravenously 1 day and 5 days respectively after the transplantation. The mice were observed for 30 days, and the effect of the compounds evaluated in terms of the increase in life span (%) of the test mice as determined by specifying the survival days of the control mice which were administered with physiological saline solution as 100% was as shown in the following Table. Also presented are therapeutic indices of the compounds.

Increase in life span and therapeutic index in the case of i.v. administration

| | | Compound | | | |
|---|---|---|---|---|---|
| Dose (mg/kg/day) | | M-R20X | M-R20X2 | Adriamycin (Comp. data) | Aclainomycin (Comp. data) |
| Increase in life span T/C (%) | 0.25 | — | 109 | — | — |
| | 0.5 | — | 136 | — | — |
| | 1 | 104 | 154 | 103 | — |
| | 2 | 119 | 204 | 119 | — |
| | 4 | 155 | 194 | 133 | 121 |
| | 8 | 151 | 35* | 165 | 119 |
| | 12 | 57 | — | 244 | — |
| | 16 | — | — | — | 151 |
| | 32 | — | — | — | 177 |
| | 64 | — | — | — | 35* |
| Dose for T/C = 130% (mg/kg/day) | | 2.5 | 0.43 | 3.5 | 12.4 |
| Therapeutic index | | 1.6 | 4.7 | 3.4 | 2.6 |

*administered only day 1 b. Acute toxicity ($LD_{50}$)

$LD_{50}$ values of M-R20X and M-R20X2 administered to ICR mice by intravenous injection were as shown below.

| Drug | $LD_{50}$ (mg/kg) |
|---|---|
| M-R20X | 12.3 |
| M-R20X2 | 3.55 |

EXAMPLE 1

80 mg of R20X3 was dissolved in 3 cc of methanol. To the resulting solution were added 170 mg of 2,2'-oxydiacetaldehyde and 10 mg of sodium cyanoborohydride as a reducing agent, and the mixture was subjected to reaction at room temperature for one hour.

To the reaction mixture was added 100 cc of water, and the resulting mixture was extracted three times with 100 cc of chloroform. The extract thus obtained was washed with water and thereafter applied to silica gel column chromatography for separation. More particularly, the extract was first developed with a chloroform: methanol = 50: 1 solvent system and then with a chloroform: methanol = 10: 1 solvent system. M-R20X3 was eluted with this chloroform: methanol = 10: 1 solvent system and, by concentration thereof, 16 mg of M-R20X3 was obtained.

EXAMPLE 2

80 mg of R-20X3 was dissolved in 1 cc of methanol. To the resulting solution were added 170 mg of 2,2'-oxydiacetaldehyde and 10 mg of sodium cyanoborohydride, and the mixture was stirred for one hour at room temperature. To the resulting mixture were added 20 μl of a 2.8% ("w/v%" as in all percentages set forth hereinafter) aqueous ammonia and then 6 cc of acetone, and the mixture was stirred for one hour. To this solution was added 100 cc of water, and the resultant solution was extracted with chloroform. The chloroform layer was dehydrated, concentrated and developed with a chloroform: methanol = 50: 1 solvent system in silica gel column chromatography to obtain 6.0 mg of M-R20X2 and 1.5 mg of M-R20X.

Reference Example 1 (Production of R20X3)

R20X3 was produced from strain R20 by the process described hereinbelow.

(1) Inoculum Preparation

A medium used to grow a primary inoculum was prepared by dissolving the following ingredients in 1 liter of water and adjusting the pH of the resultant solution to 7.2.

| Polypeptone | 1% |
|---|---|
| Molasses | 1% |
| Meat extract | 1% |

100 ml of the medium thus prepared was sterilized in a 500-ml Erlenmeyer flask and inoculated with a loopful of spores collected from a slant culture of strain R20. The inoculated medium was subjected to shake culture for 5 days at 27° C. on a rotary shaker (200 r.p.m.) to prepare an inoculum.

(2) Cultivation

A fermentation medium was prepared by dissolving the following ingredients in 1 liter of water and adjusting the pH of the resultant solution to 6.5.

| Glucose | 0.5% |
|---|---|
| Corn steep liquor | 1.5% |
| Soybean meal | 1.5% |
| Maltose | 4.0% |
| Dry yeast | 0.2% |
| Calcium carbonate (precipitated) | 0.4% |

25 liters of the fermentation medium thus prepared was sterilized in a 50-l jar fermenter and inoculated with 3 vials of the inoculums prepared as described above. The fermentation was carried out at 27° C. for 7 days at 1 v.v.m. and 200 r.p.m.

(3) Recovery of R20X3

After the fermentation, the fermented mash was adjusted to pH 10.0 with 1N aqueous ammonia and filtered to separate cells from the filtrate which was adjusted to pH 2.0 with 4N hydrochloric acid. The precipitate formed was subjected to centrifugation to obtain 7.8 g of crude R20X3 powder. This crude powder was applied to silica gel column chromatography using a chloroform: methanol: water (100: 10: 0.1) solvent system, and the R20X3 fraction eluted was concentrated. To the residue thus obtained was added a 1% sodium hydrogencarbonate solution, and chloroform was further added to the mixture to extract the ingredients except R20X3. The aqueous layer was washed with chloroform and adjusted to pH 2 with 4N hydrochloric acid, and thereafter R20X3 was extracted with n-butanol. The butanol layer was washed with water several times and then concentrated to obtain 2.3 g of R20X3.

The physiocochemical properties of the R20X3 thus obtained were as follows and found to fully conform to the data reported in Japanese patent laid-open pub. No. 8300/1985 and Journal of Antibiotics, 39 (30), 473(1985).

(1) Melting point: 165°–166° (decomposed)
(2) Specific rotatory power:
$[\alpha]_D^{25} = +185°$
(C=0.1, in methanol)
(3) Ultraviolet and visible absorption spectrum:
$\lambda_{max\ nm}$ ($E_{1\ cm}^{1\%}$):
234 (601), 257 (410),
495 (225), 530 (159)
(4) Infrared absorption spectrum (KBr):
1710 cm$^{-1}$, 1600 cm$^{-1}$
(5) Behavior as observed by thin-layer chromatography (on silica gel TLC plate 60F$_{254}$ supplied by Merck & Co., Inc.)

| Chloroform:Methanol:Acetic acid:water | Rf |
|---|---|
| 80:20:0.5:0.5 | 0.45 |

(6) Proton nuclear magnetic resonance spectrum (in deuterochloroform-deuteromethanol):

| | |
|---|---|
| 1.13 | (3H, t, J=7.0 Hz, H-14) |
| 1.30 | (3H, d, J=6.3 Hz, H-6') |
| 1.55 | (1H, m, H-13a) |
| 1.80 | (1H, m, H-13b) |
| 1.70–2.35 | (4H, m, H-2', H-8) |
| 3.70 | (1H, brs, H-4') |
| 4.19 | (1H, s, H-10) |
| 4.23 | (1H, q, J=6.3 Hz, H-5') |
| 5.10 | (1H, brs, H-7) |
| 5.47 | (1H, brs, H-1') |
| 7.14 | (1H, d, J=8.0 Hz, H-3) |
| 7.56 | (1H, dd, J=8.0 Hz, 8.0 Hz, H-2) |
| 7.60 | (1H, d, J=8.0 Hz, H-1) |

Reference Example 2

16 mg of M-R20X3 was dissolved in 3 cc of acetone, and the solution obtained was stirred for 4 hours at room temperature. The resulting solution was concentrated and developed with a chloroform: methanol=50: 1 solvent system in silica gel column chromatography to obtain 2.4 mg of M-R20X2 and 2.0 mg of M-R20X.

Reference Example 3

16 mg of M-R20X3 was dissolved in 3 cc of dimethylformamide, and the solution obtained was stirred for 4 hours at room temperature. The resulting solution was concentrated in vacuo and developed with a chloroform: methanol=50: 1 solvent system in silica gel column chromatography to obtain 4.5 mg of M-R20X2.

Reference Example 4

To 16 mg of M-R20X3 was added 0.5 cc of a 2.8% aqueous ammonia, and was further added 3 cc of acetone dropwise. The mixture was stirred for 4 hours at room temperature, concentrated, and developed with a chloroform: methanol=50: 1 slvent system in silica gel column chromatography to obtain 3.8 mg of M-R20X2 and 1.0 mg of M-R20X.

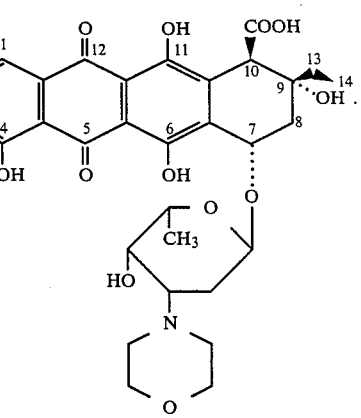

What is claimed is:

1. An anthracycline compound of the following formula or an acid addition salt thereof: